Figure 1:
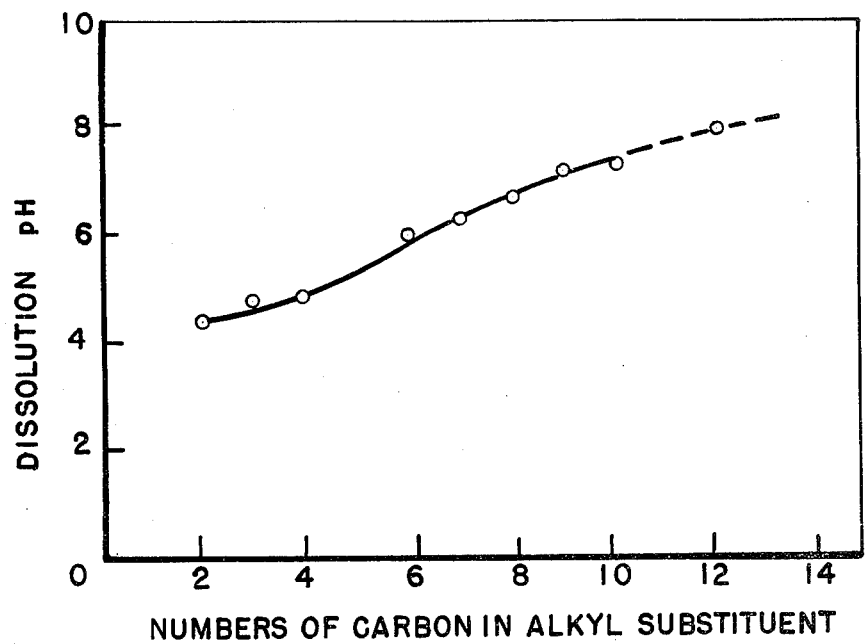

United States Patent [19]

Heller

[11] 4,261,969

[45] Apr. 14, 1981

[54] CONTROLLED DRUG RELEASE COMPOSITION

[75] Inventor: Jorge Heller, Palo Alto, Calif.

[73] Assignee: World Health Organization, Geneva, Switzerland

[21] Appl. No.: 35,639

[22] Filed: May 3, 1979

[51] Int. Cl.³ .................... A61K 9/02; A61K 31/17; A61K 37/48; A61K 31/74

[52] U.S. Cl. .................... 424/19; 424/22; 424/33; 424/94; 424/322

[58] Field of Search .................... 424/19, 33, 94, 322

[56] References Cited

U.S. PATENT DOCUMENTS

| | | | |
|---|---|---|---|
| 650,760 | 5/1900 | Metcalf | 424/37 |
| 671,804 | 4/1901 | Metcalf | 424/37 |
| 1,661,588 | 3/1928 | Neergaard | 424/322 |
| 2,460,776 | 2/1949 | Vincent | 424/322 |
| 2,743,208 | 4/1956 | Marcose et al. | 424/322 |
| 2,840,506 | 6/1958 | Goodfriend | 424/322 |
| 2,859,113 | 11/1958 | Goodfriend | 424/322 |
| 3,108,043 | 10/1963 | Millman et al. | 424/322 |
| 3,138,535 | 6/1964 | Heim | 424/322 |
| 3,143,472 | 8/1964 | Lappas et al. | 424/33 |
| 3,164,519 | 1/1965 | Peutzor | 424/322 |
| 3,181,998 | 5/1965 | Kanig | 424/94 |
| 3,407,157 | 10/1968 | Cartenson et al. | 424/33 |
| 3,452,135 | 6/1969 | Medveczky | 424/322 |
| 3,452,138 | 6/1969 | Granatok et al. | 424/322 |
| 3,493,652 | 2/1970 | Hartman | 424/94 |
| 3,531,563 | 9/1970 | Klothen et al. | 424/322 |
| 3,644,642 | 2/1972 | Wilson et al. | 424/322 |
| 3,666,863 | 5/1972 | Swanbeck | 424/322 |
| 3,705,239 | 12/1972 | Gregory | 424/322 |
| 3,751,561 | 8/1973 | Wildi et al. | 424/94 |
| 3,842,022 | 10/1974 | Wang | 424/322 |
| 3,909,444 | 9/1975 | Anderson et al. | 424/33 |
| 3,914,401 | 10/1975 | Sharabash | 424/33 |
| 3,981,996 | 9/1976 | Leigh | 424/322 |
| 4,004,979 | 1/1977 | Auramsas et al. | 424/94 |
| 4,035,479 | 7/1977 | George et al. | 424/322 |
| 4,045,244 | 8/1977 | Lange | 424/322 |

FOREIGN PATENT DOCUMENTS

| | | | |
|---|---|---|---|
| 1588756 | 7/1966 | France | 424/322 |
| 2035774 | 12/1970 | France | 424/94 |
| 40-3274 | 2/1965 | Japan | 424/94 |
| 49-25128 | 3/1974 | Japan | 424/94 |
| 865770 | 4/1961 | United Kingdom | 424/322 |
| 1404583 | 9/1975 | United Kingdom | 424/322 |

OTHER PUBLICATIONS

Sax Handbook of Dangerous Materials, (1951), pp. 17–18, Ammonia, Anhydrous, Reinhold Publ. Co., N.Y., N.Y.

Thompson, "A Study of Enteric Coatings", (RS201A2T4), Thesis–Purdue University, Sep. 1944, pp. 3, 4, 10, 11, 12, 27, 28, 43, 44, 85 & 86.

Primary Examiner—Shep K. Rose
Attorney, Agent, or Firm—Cushman, Darby & Cushman

[57] ABSTRACT

A novel, closed loop drug delivery system has been developed where the presence or absence of an external compound determines delivery of a drug from a bioerodible polymer. In the described delivery system hydrocortisone is incorporated into a n-hexyl half ester of a methyl vinyl ether-maleic anhydride copolymer and the polymer-drug mixture fabricated into discs. These are then coated with a hydrogel containing immobilized urease. In a medium of constant pH and in the absence of external urea, the release of hydrocortisone is that normally expected for that polymer at the given pH. In the presence of external urea, ammonium bicarbonate and ammonium hydroxide is generated within the hydrogel which accelerates polymer erosion and hence drug release. Drug delivery rate increase is proportional to the amount of external urea and is reversible, that is, when external urea is removed, the rate of drug release gradually returns to its original value.

1 Claim, 7 Drawing Figures

RELATIONSHIP BETWEEN pH OF PRECIPITATION & SIZE OF ESTER GROUP IN HALF ESTERS OF METHYL VINYL ETHER-MALEIC ANHYDRIDE COPOLYMERS.

RELATIONSHIP BETWEEN pH OF PRECIPITATION & SIZE OF ESTER GROUP IN HALF ESTERS OF METHYL VINYL ETHER-MALEIC ANHYDRIDE COPOLYMERS.

RATE OF POLYMER DISSOLUTION & RATE OF RELEASE OF HYDROCORTISONE ALCOHOL FOR THE n-BUTYL HALF ESTER OF METHYL VINYL ETHER-MALEIC ANHYDRIDE COPOLYMER CONTAINING 10 WT% DRUG DISPERSION.

FIG. 3
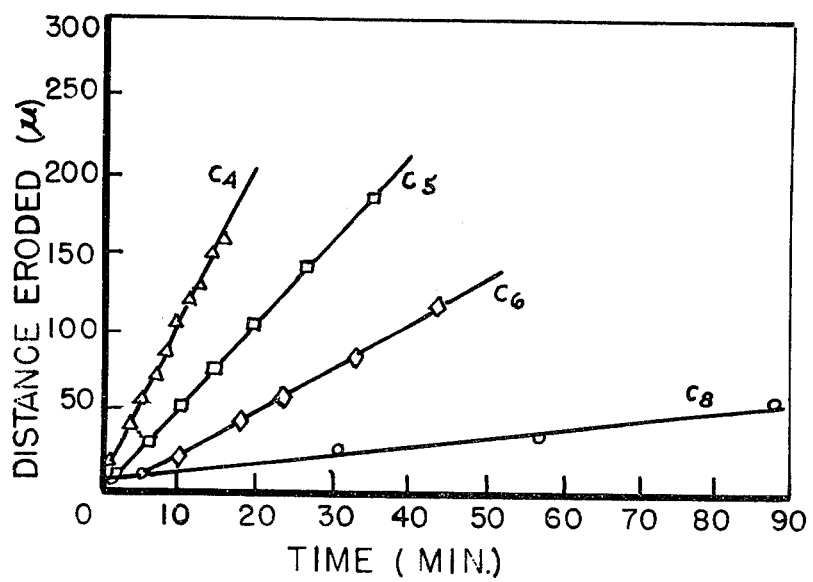
EFFECT OF SIZE OF ESTER GROUP IN HALF ESTERS OF METHYL VINYL ESTER-MALEIC ANHYDRIDE COPOLYMERS ON RATE OF EROSION AT pH 7.4.
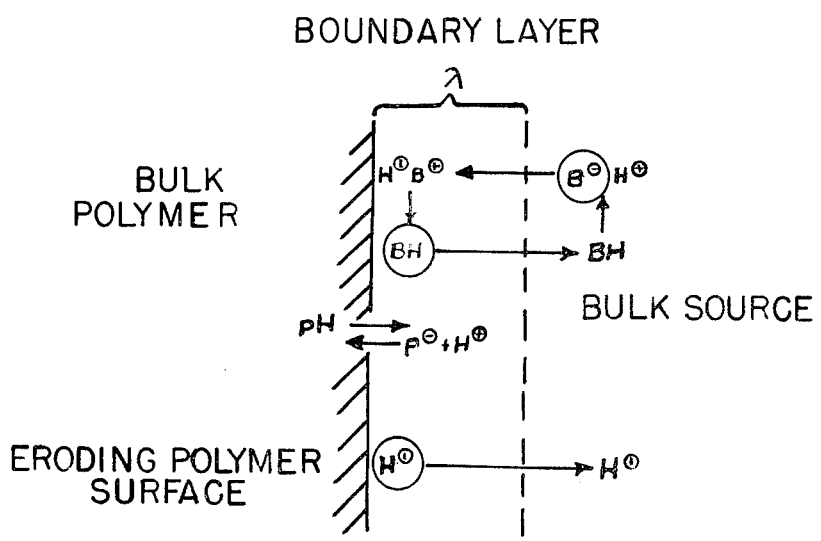
FIG. 5

EFFECT OF pH OF EROSION MEDIUM ON RATE OF EROSION OF HALF ESTERS OF METHYL VINYL ETHER-MALEIC ANHYDRIDE COPOLYMERS.

CONTROLLED DRUG RELEASE COMPOSITION

The present invention is concerned with a controlled release composition which is capable of delivering an active agent, for example, a drug, in an amount responsive to the body's need for such agent.

It is well recognized that systems which deliver an active agent to a specific body site in a precisely regulated amount are vastly superior to those that indiscriminately flood the whole body with a therapeutic agent whose site of action is specific. Furthermore, even with therapeutic agents not destined for a specific site, definite advantages can be derived from a precisely controlled delivery since a longer therapeutically-effective regime can be achieved with less drug than is the case with conventional medication.

Considerable attention has been directed towards developing improved drugs delivery systems which provide for sustained, precisely controlled drug release (see Baker and Lonsdale, Chemtech 5, 668, 1975) and quite a number of methods and systems have been proposed as useful for this purpose.

However, even precisely controlled sustained delivery is not always the optimum therapeutic regime because in many applications the better delivery system, if available, would be one which delivers the active agent in precisely controlled amount but only when needed. Because the body is a complex system which undergoes cyclic changes, such as menstrual cycles or the so-called circadian biochemical rhythms, an ideal delivery system would be one that delivers a therapeutic agent in concert with these changes. Such a cyclic delivery, patterned after a well-defined cycle, can in theory be achieved with layered devices using the so-called "on-ion" system wherein alternate layers of drug-laden and nondrug-laden surface-eroding polymers are employed. However, aside from the obvious difficulties of fabricating such products, preventing diffusion of drug from one layer to another, and assuring absolutely even erosion, the delivery pattern is rigidly fixed and is really independent of the recipient's cyclic needs. Furthermore, since it is highly questionable that such a delivery system can remain coupled to the body's cyclic need for long periods of time, it is not likely that a product based on the "onion" system can be effectively used to release a controlled amount of an active agent in the body according to the body's need for that agent. Consequently, there exists a real need for a controlled release composition which will release a drug or other active agent according to the body's requirements.

The principal object of the present invention is to provide a purely chemical system, namely, an enzyme-mediated polymer composition, which is capable of releasing a drug or the like in the body in carefully controlled amounts and only on an as-needed basis. Other objects will also be hereinafter apparent.

Broadly stated, the drug delivery system of the invention comprises (1) sensing means which can detect and measure small amounts of a specific compound in complex mixtures such as blood and/or other body fluids which is an indicator of the body's need for the drug; and (2) means of transferring the sensed information to a delivery component that is then able to deliver the therapeutic agent in the amount needed. While it is possible to visualize electromechanical systems, for example, micro electronics and/or enzyme process control miniaturized pumps, there are special advantages to having a purely chemical system, as in the present case, to accomplish the indicated purpose. For example, the system of the present invention offers a more convenient means for use as a contraceptive where the contraceptive drug is released only when needed than possible alternatives involving mechanical or electromechanical devices.

The drug delivery composition of the invention may be described as comprising:

(1) a bioerodible hydrophobic polymer containing the drug or other active agent and having an erosion rate that is highly pH sensitive in aqueous medium and (2) an immobilized enzyme-containing layer surrounding or encasing the polymer (1), the enzyme being such that it will react with a selected external trigger molecule indicative of the condition to be treated in such a way that a pH change takes place which directly affects polymer erosion and hence release of the active agent.

In essence, the invention provides a "closed loop" system, i.e. a drug delivery composition whose output of active agent is directly coupled to a specific physiological condition as reflected by the presence of a trigger compound in the environment where the system is used. Release of the drug or active agent is proportional to the amount of trigger compound present in the environment and when none is present, the drug release stops.

The essence of the invention involves coupling together two known phenomena: (a) drug release from polymers whose erosion rate is strongly pH dependent, and (b) enzyme-substrate (i.e. trigger compound) reactions that produce pH changes. The invention is based on the finding that these two phenomena can be successfully coupled and that enzyme induced pH changes of sufficient magnitude to affect useful polymer dissolution and consequent drug release can be obtained.

As indicated, it is essential to the invention that the erodibility of the polymer used herein be significantly pH-dependent, i.e. the polymer selected for use should be one wherein solubility in aqueous medium, e.g. in body fluids, changes relatively sharply with a small pH change (e.g. a pH change of 0.25 or even less).

Preferred polymers suitable for use herein are described in U.S. Pat. Nos. 3,811,444 and 4,014,987 and a paper entitled "Controlled Drug Release by Polymer Dissolution" by Heller et al, Journal Applied Polymer Science, 22, 1991 (1978), hereinafter referred to as the "Heller et al" paper and incorporated herein by reference. These polymers comprise partially esterified copolymers of ethylene or methylvinyl ether and maleic anhydride. The preesterified copolymers are commercially available as, for example, Gantrez AN-169 (GAF Corp., New York, New York) and they may be partially esterified for present purposes as follows:

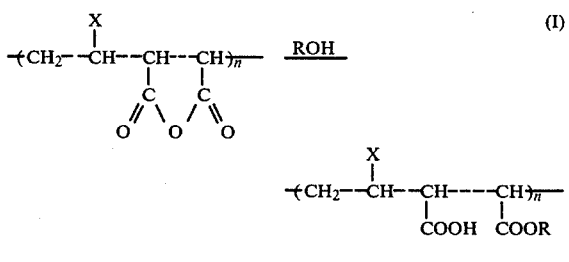

where $X = OCH_3$ for the methyl vinyl ether copolymer or $X = H$ for the ethylene copolymer, R is alkyl and n is an integer representing the number of repeat units in the polymer. The value of n should be sufficient to give a film-forming polymer.

These copolymers (I) in the unionized state are hydrophobic and water insoluble, and in the ionized state they are water soluble. They exhibit a characteristic pH above which they are soluble and below which they are insoluble. This pH is quite sharp (about 0.25 pH units) and changes linearly with the number of carbon atoms in the ester side group. This linear relationship is shown in FIG. 1.

This solubility behavior can be understood by recognizing that polymers with small ester groups (short chain alkyl) are relatively hydrophilic but become progressively more hydrophobic as the size of the ester group increases. Since the pKa of the acid is relatively insensitive to the size of the alkyl group, it follows that the behavior depicted in FIG. 1 indicates the necessity for a progressively higher degree of ionization before the polymer can be solubilized. Hence, dissolution takes place at progressively higher pH values as the alkyl ester group increases in size.

Figure 2:
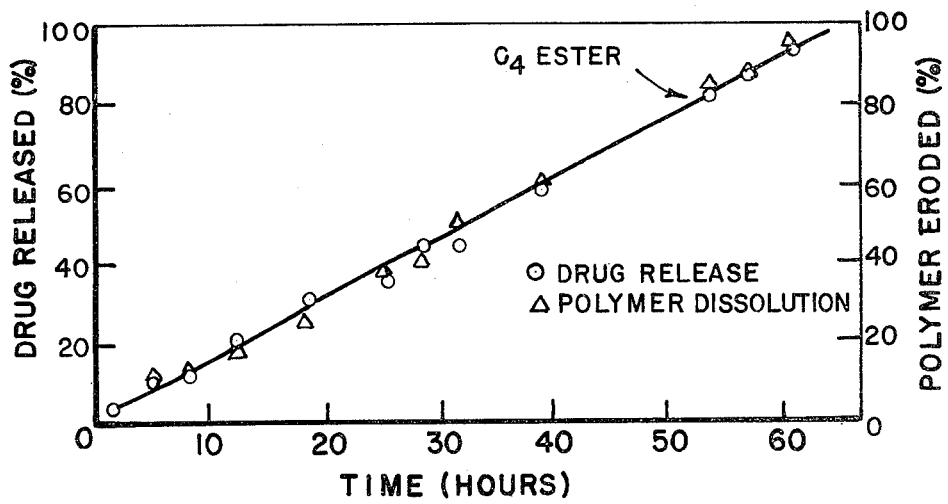

FIG. 2 shows polymer dissolution rate and rate of hydrocortisone release for n-butyl half ester polymer films containing the dispersed drug. Each pair of points represents a separate composition where the amount of drug released by the composition into an aqueous wash solution was determined by UV measurements and where the amount of polymer dissolved was calculated from the total weight loss of the composition. The excellent linearity of both polymer erosion and drug release over the total lifetime of the composition provides strong evidence for a surface erosion mechanism and negligible diffusional release of the drug. The latter result has been verified by placing a drug-containing film in water at a pH low enough to ensure that no dissolution of the polymer matrix takes place and periodically analyzing the aqueous solution for hydrocortisone. None was found over a period of several days.

FIG. 3 shows the effect of the size of the alkyl group on the rate of release of hydrocortisone for a series of partial esters measured at pH 7.4. All drug release rates again show excellent linearity and also show a strong dependence on the size of alkyl group. Since in all experiments depletion of drug also coincided with total polymer dissolution, it can be assumed that drug release and polymer erosion occur concomitantly.

Figure 4:
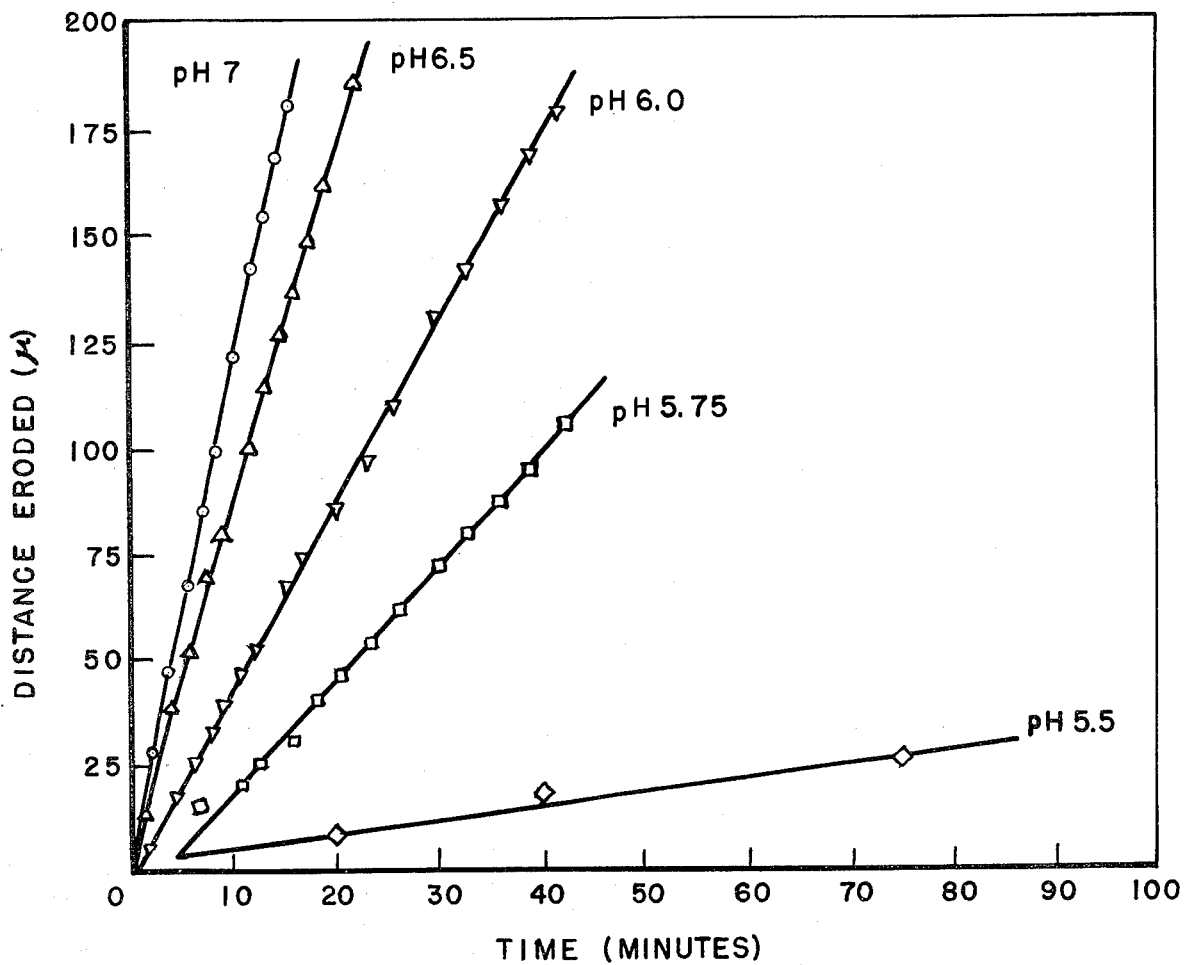

The effect of pH on the rate of release of hydrocortisone dispersed in the n-butyl partial ester is shown in FIG. 4. The data show a clear dependence of the erosion rate and the drug release on the pH of the eroding medium and, as expected, a progressive decrease in rate as the critical dissolution pH is approached.

To summarize, the copolymers I are characterized by: (1) the ability to undergo surface erosion and hence release an incorporated drug by zero order kinetics; (2) an extraordinary sensitivity of the erosion rate to the pH of a surrounding aqueous environment; and (3) a characteristic pH above which they are completely soluble and below which they are completely insoluble. This pH is very sharp and depends on the size of the alkyl group in the ester portion of the copolymer. Consequently, the erosion behavior of the polymer can be tailored to fit any desired pH environment, and even very small variations of that pH can have a major effect on erosion rate, and thus on drug release.

While the Heller et al paper discloses the concept of drug release by surface erosion or dissolution of a polymer on the basis of pH variations, the paper does not describe an essential feature of the present invention, i.e. the sensing mechanism associated with the polymer which responds to the presence of a specific compound in the external environment so as to bring about a pH change which can be used to control polymer dissolution and hence delivery of the drug or therapeutic agent. The invention contemplates using for the sensing mechanism, any agent which will react with a particular trigger compound when the compound occurs externally in the environment surrounding the polymer to give a reaction product that changes the pH to a point where the polymer is soluble or erodible and will erode with liberation of the drug carried thereby. Then, when the trigger compound is no longer present, no further reaction occurs and erosion of the polymer discontinues.

Enzymes are the preferred sensing agents because their mode of action is highly specific and in many cases the reaction products of the enzyme-substrate (trigger compound) reaction are acidic or alkaline compounds. Typically, the enzyme may be urease which will react with urea as the trigger compound, in aqueous medium as known (Blakeley et al, Biochemistry, 8, 1991 (1969) according to the following reaction:

The basic mode of the enzyme action can be described by the Michaelis-Menton equation for enzyme kinetics:

As shown, enzyme E combines with substrate (trigger compound) S to form an intermediate complex ES, which subsequently breaks down into product P and the original enzyme E. For present purposes, the enzyme must be one which, after reaction with the substrate, liberates a product that is alkaline so that the net effect is a pH increase at the polymer/water interface.

The invention is illustrated by the following example wherein urease is used as the enzyme, urea as the trigger compound, hydrocortisone as the drug and the n-hexyl half ester of methyl vinyl ether/maleic anhydride copolymer as the polymer matrix. The n-hexyl ester was selected because the polymer system should be one which erodes at a pH value higher than 7.4, the biological pH, and this requires an ester group with at least 6 carbon atoms (see FIG. 1). Urea is reasonably representative of a prospective trigger compound while urease is desirable to use as the enzyme because it is enormously efficient and has a $k_{cat}$ for the hydrolysis of urea that is about two orders of magnitude greater than the $k_{cat}$ for any peptidase in the hydrolysis of other carboxyamides. This enormous efficiency can be better appreciated if one considers that 1 g of highly purified urease can produce as much as 60 g of ammonia in 5 min. Thus, a relatively small amount of urease in the polymer matrix can lead to substantial changes in pH at the polymer-water interface.

EXAMPLE

(1) Preparation of n-hexyl Half-ester of a 50/50 Copolymer of Methyl Vinyl Ether and Maleic Anhydride[1]

A three-neck 2000 ml round-bottom flask equipped with a mechanical stirrer, heating oil bath, condensor, and nitrogen inlet and exit was charged with 109.30 gm of the copolymer (1.400 equivalent) and 794.82 gm of n-hexyl alcohol (7.779 mole). The alcohol was present in a 11/1 molar excess and is sufficient to produce a 20% by weight solution of the half-ester product.

[1] Gantrez AN-169, GAF Corp., New York, New York.

After purging the flask with nitrogen, the reactants were vigorously stirred and heated over a half-hour period to 145° C. The course of the reaction was followed by IR analysis of the carbonyl peaks associated with residual cyclic anhydride in the copolymer and with the formed ester linkage in the half-ester product. The reaction was judged complete after 2½ hours at 145° C. The solution was cooled to room temperature with an ice-bath and precipitated in 8000 ml of a mixture of methanol/water (1:1 by volume). The precipitated polymer was dissolved in 2000 ml of acetone and precipitated in 8000 ml of a mixture of methanol/water (1:2 by volume). This step was repeated two more times. The product was dried in a forced-air oven for three days at 50° C. 148.10 gm of a tough, clear-to-slightly-hazy material was collected at a yield of 82%.

(2) Preparation of Test Specimens

(a) Casting of Films

The polymer and micronized hydrocortisone[2] were added to a mixture of cellosolve acetate/methyl isobutyl ketone (7:3 by weight) to produce a 9 wt% polymer solution containing 10 parts of dispersed hydrocortisone per hundred parts of resin. A homogeneous solution was obtained by using a jar-mill. Films were cast by pouring this solution into level teflon-lined molds. The molds were then partially covered and, to prevent formation of bubbles in the film, dried slowly for eight days. It was further dried in a forced-air oven at 35° C. for one day and then in vacuo for one day.

[2] Upjohn, Kalamazoo, Michigan

Discs, 9.5 mm in diameter, were cut from the film, using a drill press and hole cutter. The discs were weighed after being placed in a vacuum oven for 48 hours at room temperature and then equilibrating to constant weight in air. The discs selected for released-rate testing weighed between 47.5 mg and 52.5 mg and were approximately 0.75 mm thick.

(b) Enzyme Coating

Initial attempts to incorporate the enzyme urease into the polymer matrix involved dissolving the enzyme and polymer in acetone, then dispersing micronized hydrocortisone in the solution, casting films and gently drying at room temperature. However, considerable denaturation of the enzyme took place. Accordingly coupling of the urease to the polymer matrix was based on the work of Mascini and Guibault[3] and was carried out by the following procedure: A small locking forceps was affixed to the edge of each polymer disc so that the disc could be manipulated without touching the surfaces during the immobilized enzyme-coating procedure. A 30% aqueous solution of bovine-serum albumin was prepared and to 10 ml of this solution was added 1 gm of urease. After quick stirring until the urease had dissolved, the solution was chilled in an ice-bath. Each disc was held horizontally by the attached forceps and one drop of the albumin-urease solution was added to the upper face of the disc. The disc was quickly rotated and a drop was added to the opposite face. Similarly, one drop of 25% aqueous glutaraldehyde was added to each face of the disc. One minute after adding the glutaraldehyde, the coating had gelled sufficiently to allow the discs to be hung vertically.

[3] Anal. Chem., 49, 795 (1977)

After standing in air for 15 minutes, the coated discs were immersed in cold, deionized water for 15 minutes, then in 0.1 M glycine solution for 15 minutes, then in pH 5.75 phosphate buffer solution for 2 hours. Finally they were immersed in fresh pH 5.75 phosphate buffer solution for 4 hours.

(3) Release Rate Measurements

The coated discs were heat-sealed in polypropylene mesh bags having 0.5 mm openings. Care was taken to apply heat only to the edges of the bags and to avoid applying heat to the discs. The mesh bags were then attached to 10-gauge stainless steel wires and moved vertically up and down at ~140 cm/min in test tubes (i.e. approximately 18.4 cycles/min at a total sample travel distance of 7.62 cm/cycle as described in the previously mentioned Heller et al paper. Release of hydrocortisone was followed spectrophotometrically at 242 nm.

(4) Results and Discussion

The Heller et al paper describes the erosion behavior of a hydrophobic polymer system where dissolution occurs by the ionization of carboxyl groups. This solubilization behavior has been generally represented as follows:

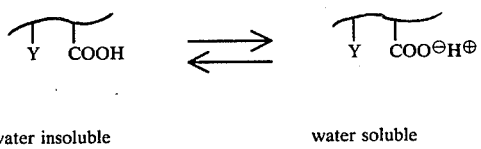

water insoluble          water soluble where COOH is a solubilizing group and Y is a hydrophobic substituent. The dissolution behavior can be rationalized in terms of the model shown in FIG. 5. In this model the rate of erosion is principally determined by the rate at which hydrogen ions are neutralized within the boundary layer, so that induced pH change in that layer will have a significant effect on polymer erosion, and hence drug release.

In the system exemplified in the foregoing example, the hydrophobic n-hexyl half-ester of a methyl-vinyl-ether maleic anhydride copolymer containing hydrocortisone is surrounded by a hydrogel consisting of the enzyme urease, immobilized in bovine-serum albumin by crosslinking with glutaraldehyde. In the presence of external urea, the rate of polymer dissolution and hence release of hydrocortisone occurs by the mechanism shown in FIG. 5, that is, hydrogen ion neutralization by external buffer (B) and diffusion of hydrogen ions away from the eroding polymer.

When urea is present in the external environment, it will diffuse into the hydrogel layer and be converted to ammonium bicarbonate and ammonium hydroxide by the immobilized urease. These basic species will now neutralize hydrogen ions generated by the eroding polymer, thus accelerating the process. Consequently, presence of urea in the external environment should lead to accelerated drug release, and this acceleration should be directly proportional to the concentration of external urea. The data in FIG. 6 corroborate these expectations.

It is to be noted that while care was taken to maintain constant pH in the external environment, this was accomplished only with $10^{-2}$M urea. In the presence of $10^{-1}$M urea, generation of basic species was so rapid that the buffering capacity of the external medium was exceeded and a pH increase of about 0.25 occurred. Furthermore, the rate of polymer dissolution was such that when the solubilized polymer chains diffused through the hydrogel, presumably through open pores, they precipitated again when exposed to the lower external pH. Because of the considerable difference in polymer dissolution rates between the hydrogel and the bulk solution, the compositions gradually acquired a significant thickness of precipitated gelatinous polymer. Nevertheless, even though a rigorous comparison between no urea and urea is possible only in the $10^{-2}$M case, there is no question that in the presence $10^{-1}$M urea the composition delivers hydrocortisone significantly faster than in the presence $10^{-2}$M urea.

Figure 6:
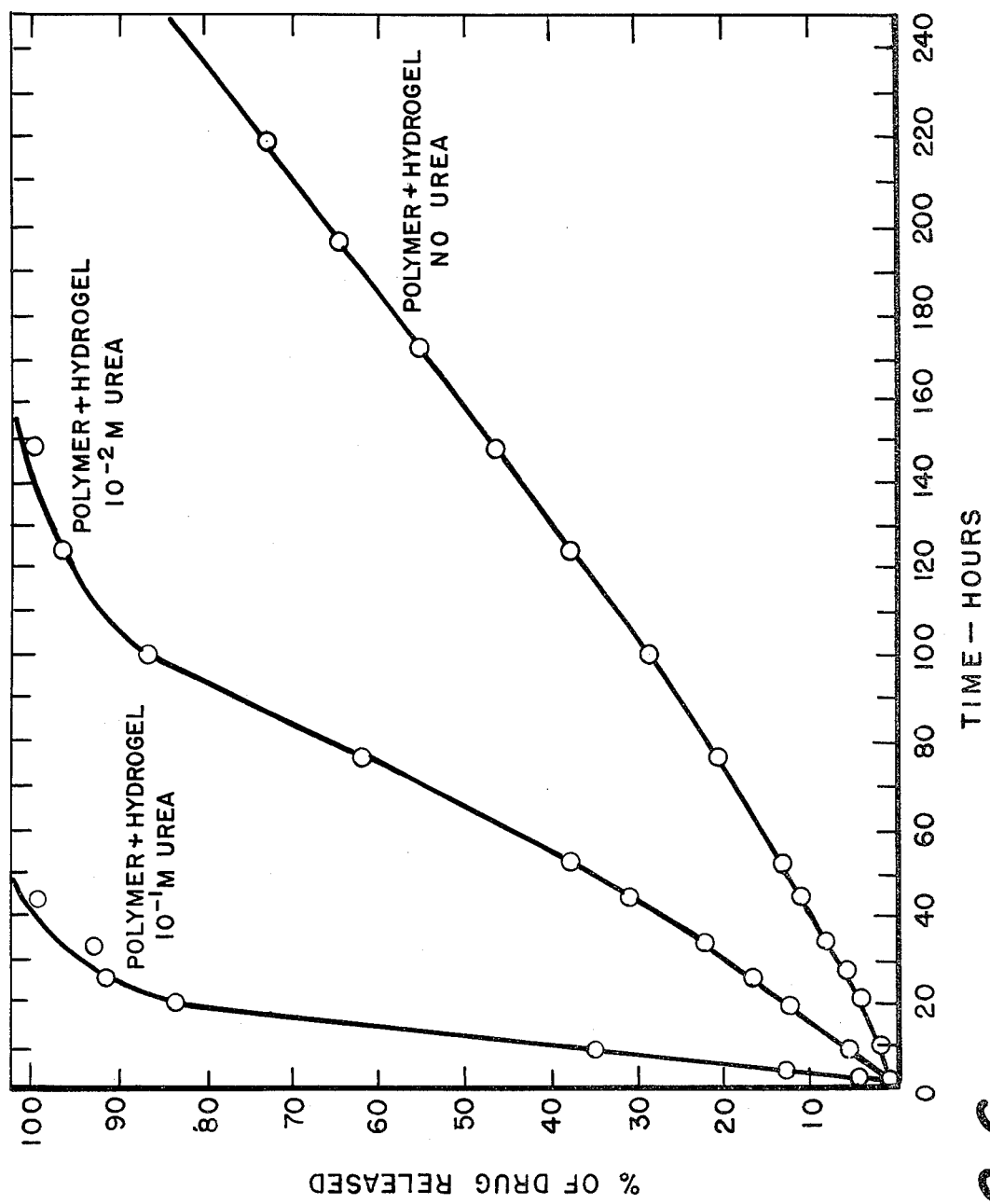

The data shown in FIG. 6 illustrate a situation where a product according to the invention has a fixed and constant rate of drug delivery that increases in response to the presence and concentration of external urea. More specifically, FIG. 6 shows the rate of hydrocortisone release at 35° C. from a n-hexyl half-ester of a copolymer of methyl vinyl ether and maleic anhydride prepared as described above, at pH 6.25 in the absence and presence of external urea. The stirring rate is ~140 cm/min.

Figure 7:
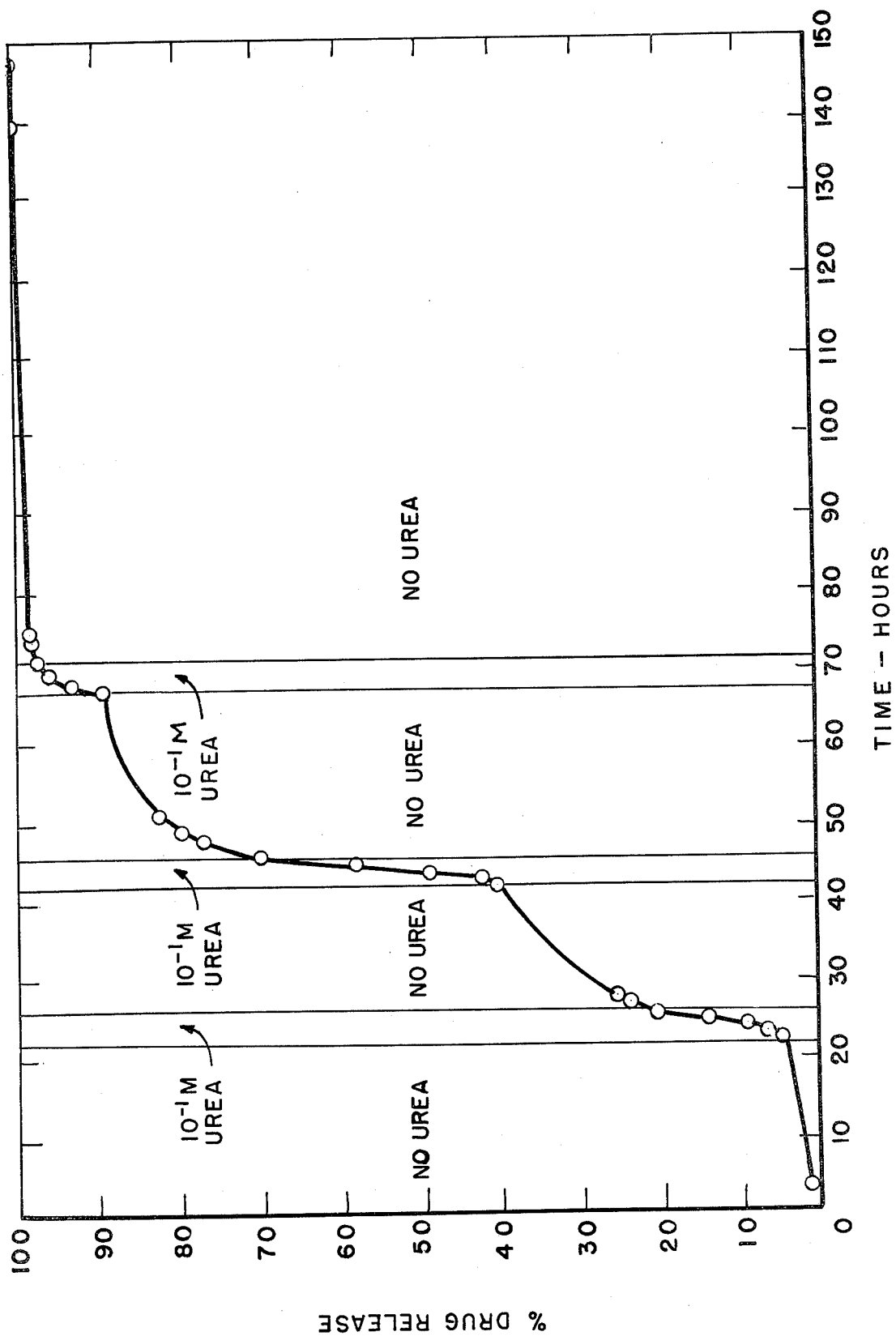

FIG. 7 shows the results of experiments to see if the situation presented by FIG. 6 is reversible so that the rate of delivery will return to its original value when the trigger component is removed. More specifically, FIG. 7 shows the rate of hydrocortisone release at 35° C. from a n-hexyl half-ester of a copolymer of methyl vinyl ether and maleic anhydride prepared as described above at pH 6.25 as a function of sequential addition and removal of $10^{-1}$M urea. The stirring rate is ~140 cm/min. As indicated earlier, polymer erosion in the presence of $10^{-1}$M urea is so rapid that polymer precipitates. Nevertheless, the data clearly show that when the delivery system is removed from a buffer solution without urea and placed in a buffer solution with $10^{-1}$M urea, a significant increase in delivery immediately takes place. When the delivery system is next removed from that solution and again placed in a solution without urea, a decrease of delivery rate takes place. The decrease in delivery is not abrupt, but instead shows a first order dependence. This first order dependence is a consequence of the relatively water-insoluble hydrocortisone being trapped in the hydrogel layer and in the precipitated polymer around the device from which it is slowly released by a diffusional mechanism, when the device is in the low rate erosion regime. In the high rate delivery regime, a zero order delivery is noted because the slow diffusional release is masked by the very rapid erosional release.

As will be evident, the drug delivery system of the invention consists of a water-sensitive hydrophobic polymer containing within its matrix a dispersed or dissolved drug with a relatively low water solubility. The reaction between the polymer and the aqueous environment is confined to the polymer-water interface and diffusional release of the drug is minimal, so that zero-order release kinetics are achieved, there being no significant change in the total area of the composition with time. The system is suitable for use as a generic delivery system to release various drugs as needed at a preselected delivery rate by controlling the polymer dissolution rate according to pH.

Stated somewhat differently, the invention provides an erodible composition for the controlled delivery of a predetermined active agent to a surrounding aqueous medium. The composition comprises an active agent dispersed within a substrate or body of a selected hydrophobic polymer whose erosion rate is highly pH-dependent. The hydrophobic polymer is surrounded by a layer containing an immobilized enzyme so chosen that it interacts with a specific external compound to produce a marked pH change. This pH change directly affects the erosion of the hydrophobic polymer and, as a result, the delivery of the active agent incorporated therein. The enzyme-substrate interaction thus gives a composition which dispenses active agent to the surrounding medium only in response to the presence of a predetermined specific external compound and in a way which is directly proportional to the concentration of the external compound.

While the system illustrated in the foregoing example serves as a useful model to demonstrate the nature of the invention, it will be appreciated that the fundamental concepts of the invention can be applied to a variety of combinations of polymers and enzymes which meet the requirements prescribed herein to release a drug or the equivalent in a controlled amount based on need. Clearly, the enzyme should be selected according to the nature and type of external compound or trigger agent which is indicative of the condition to be treated by the drug release and which will react with the enzyme to give the pH change needed to bio-erode the polymer for drug release. Thus, the compositions can be specifically tailored to fit the conditions and needs for the treatment of interest. The polymer can be selected on the basis of its solubility characteristics at the pH anticipated when the enzyme or other sensing component reacts with the selected trigger agent which is indicative of the disease or condition to be affected.

It will be evident that the drug release composition of the invention may be used in a variety of ways. For example, the drug used may be a contraceptive which is released from the polymer only as needed such as when an egg undergoes fertilization, but not otherwise. The essential thing in any case is to identify the specific agent (trigger compound) which is characteristic of the condition to be treated and have the enzyme or other sensing means react with this to change the pH and cause the polymer to erode with consequent release of the drug. It will also be recognized that the composition may be suitably shaped or otherwise adapted for its intended use, e.g. the composition may be made into a ring or other type of vaginal insert for contraceptive use.

Various modifications may be made in the invention as described herein without departing from the scope and spirit thereof as defined in the following claims wherein:

I claim:

1. A controlled release composition for use as a vaginal insert in a body which undergoes so-called circadian biological rhythym or menstrual cycles, said composition being capable of delivering a drug to the vagina of a body according to the body's need, said composition comprising (1) an alkyl half-ester of a copolymer of ethylene or methyl vinyl ether and maleic anhydride wherein the alkyl contains at least 6 carbons as a hydrophobic bioerodible polymer containing the drug and having an erosion rate that is highly pH sensitive in aqueous medium, and (2) an immobilized urease enzyme-containing hydrogel layer encasing said drug and polymer, the enzyme being such that it will react in aqueous body fluids with urea as a selected external trigger molecule indicative of the condition to be treated by the drug, the reaction being such that a pH change takes place in the aqueous body fluids adjacent the polymer which is related to the amount of trigger molecule present and which affects the polymer erosion and accordingly the rate of drug release, the drug being released only when said trigger molecule is present and then only at a rate directly proportional to the pH change reflected in said body fluid by the ammonia produced by the reaction between the trigger molecule and the urease enzyme.

* * * * *